US005561062A

United States Patent [19]

Varanelli et al.

[11] Patent Number: 5,561,062
[45] Date of Patent: Oct. 1, 1996

[54] METHOD OF INHIBITING VIRAL REPRODUCTION USING NON-PHOSPHOLIPID, PAUCILAMELLAR LIPOSOMES

[75] Inventors: Carol Varanelli, Chester, N.H.; Surendra Kumar, Vineland, N.J.; Donald F. H. Wallach, Hollis, N.H.

[73] Assignee: Micro-Pak, Inc., Wilmington, Del.

[21] Appl. No.: 265,506

[22] Filed: Jun. 24, 1994

Related U.S. Application Data

[63] Continuation of Ser. No. 5,008, Jan. 15, 1993, abandoned.

[51] Int. Cl.[6] .............................. C12N 7/06; C12N 7/04; A61K 38/54; A61K 9/127

[52] U.S. Cl. ......................... 435/238; 435/236; 424/94.3; 424/450

[58] Field of Search .................................... 435/236, 238; 424/94.3, 450

[56] References Cited

U.S. PATENT DOCUMENTS

| | | | |
|---|---|---|---|
| 4,241,046 | 12/1980 | Papahadjopoulos et al. | 424/420 |
| 4,788,146 | 11/1988 | Ring et al. | 435/101 |
| 4,789,633 | 12/1988 | Huang et al. | 435/240.2 |
| 4,911,928 | 3/1990 | Wallach | 424/89 |
| 4,917,951 | 4/1990 | Wallach | 428/402.2 |
| 5,032,457 | 7/1991 | Wallach | 436/829 |
| 5,071,648 | 10/1991 | Rosenblatt | 424/78.06 |
| 5,077,211 | 12/1991 | Yarosh | 435/193 |
| 5,147,723 | 9/1992 | Wallach | 424/89 |

FOREIGN PATENT DOCUMENTS

| | | | |
|---|---|---|---|
| 0356340 | 2/1990 | European Pat. Off. | A61K 9/50 |

OTHER PUBLICATIONS

Konopka K et al, J. Gen. Virology 71: 2899–2907 (1990).
Fraenkel–Conpat et al, *Virology*, Prentice–Hall, Inc.: Englewood Cliffs, N.J., 1982, pp. 285–289.
Nakanishi et al, Exp Cell Res, 159: 399–409, (1985).
Stegmann et al, J. Biol Chem, 261(24): 10966–9, (1986).
Klappe et al, Biochem, 25: 8252–8260, (1986).
Nir et al, Biochem, 25: 257–266, (1986).
Stegmann et al, Biochem, 24: 3107–3113, (1985).
Larsen et al, J. Gen. Virol., 71: 1947–55, (1990).
Uchida et al, Exp. Cell Res, 152: 313–321, (1984).
Yarosh et al, J. Soc. Cosmet. Chem, 41: 85–92 (Jan./Feb., 1990).
Boerner et al, Chem. Ab, 111: 28548u, (1989).
Mink, Chem. Ab., 82: 106898g, (1975).
Salganik et al, Chem. Ab., 73: 32619g, (1970).
Yoshio et al, Chem. Ab, 106: 116428g, (1987).
Amselem et al., "Fusion of Sendai virus with negatively charged liposomes as studied by pyrene–labelled phospholipid liposomes," Biochemica et Biophysica Acta, 860, pp. 301–313 (1986).
Nir et al., "Mass Action Analysis of Kinetics and Extent of fusion between Sendai Virus and Phospholipid Vesicles," Biochemistry vol. 25, No. 25 pp. 8261–8266 (1986).
Perrin et al., "Interlukin 2 Increases Protection against Experimental Rabies," Immunobiol, vol. 177, pp. 199–209 (1988).
Stegmann et al., "Membrane Fusion Activity of Influenza Virus. Effects of Gangliosides and Negatively charged Phospholipids in Target Liposomes," Biochemistry, vol. 28, No. 4, pp. 1698–1704 (1989).
Luscher–Mattli et al., "Dextran sulfate inhibits the fusion of influenza virus with model membranes, and suppresses influenza virus replication in vivo," Antiviral Research, vol. 14, pp. 39–50 (1990).
Ehara et al., "Inactivation of the Yellow Strain of Cucumber Mosaic Virus by Pancreatic Ribonuclease" *Chemical Abstracts*, vol. 106, p. 339 (Col. 1, No. 116428g), 1987.
Stegmann et al., "Fusion Activity of Influenza Virus" *Journal of Biological Chemistry*, vol. 261, No. 24, pp. 10966–10969, 1986.

*Primary Examiner*—Michael G. Wityshyn
*Assistant Examiner*—S. Saucier
*Attorney, Agent, or Firm*—Lahive & Cockfield

[57] ABSTRACT

A new method of inactivating enveloped viruses and preparations useful in accomplishing this inactivation are disclosed. The method is based on the discovery that paucilamellar lipid vesicles, preferably having non-phospholipids as their primary structural material, can fuse with enveloped virus and that the nucleic acid of the virus denatures shortly after the fusion. The method is useful for inactivating viruses such as orthomyxoviruses, paramyxoviruses, coronaviruses, and retroviruses.

7 Claims, No Drawings

METHOD OF INHIBITING VIRAL REPRODUCTION USING NON-PHOSPHOLIPID, PAUCILAMELLAR LIPOSOMES

This application is a continuation of application Ser. No. 08/005,008, filed on Jan. 15, 1993 now abandoned.

BACKGROUND OF THE INVENTION

The present invention features a method of inhibiting viral reproduction and a preparation useful for accomplishing this inhibition. More particularly, the present invention features a method of in vivo or in vitro inhibition of viral reproduction by interfering at the nucleic acid level. The method used is non-toxic to the other cells of the body and therefore has advantages relative to most chemotherapeutic viral agents.

Viruses are infectious agents having a central core of nucleic acid surrounded by an outer core of protein or lipoprotein. Viruses require a host cell as an integral part of their reproductive process. One subclass of viruses are the enveloped viruses, which act by fusion of the protein with cell membranes rather than injection of the whole virus into the cell. These enveloped viruses can have either RNA or DNA as the nucleic acid, although RNA viruses are more common. Examples of these enveloped viruses include orthomyxoviruses such as influenza virus, coronaviruses, herpesviruses, the paramyxoviruses such as Sendai and Newcastle disease viruses, retroviruses and HIV. These enveloped viruses normally have a glycoprotein/lipid exterior with "receptors" that mediate virus attachment to target cells and nucleic acid penetration into these cells. These virus envelopes are strong enough to provide effective protection to transport nucleocapsids.

One difference between the enveloped viruses, as compared with certain other viruses, is their mode of infectious activity. The enveloped viruses, which may include some retro-viruses such as HIV-1, inject the nucleic acid into the host cell by fusion of the virus lipoproteins or proteins with the cell membrane rather than penetration of the virus protein through the membrane wall. This fusion of the virus with the cell membrane is normally mediated by a fusion protein which has a structure with a high rate of preservation from species to species. *Fundamental Virology*, B. N. Fields and D. M. Knipe, editors, Raven Press, N.Y., Chapter 4, 18–23, 27–28, 33–36.

The development of phospholipid and glycolipid based lipid vesicles, generally called liposomes, was primarily as models for cell membrane structure. There has recently been an explosion in the number of papers reporting the use of these liposomes to test viral fusion. Most of this work has been carried out using either Sendai virus or Influenza A virus. For example, experiments with Influenza virus show that dextran sulphate inhibits the fusion of the virus with liposomes. See Luscher-Mattli and Gluck, *Anti-Viral Research* 14, pp. 39–50 (1990). In addition, much work has also been carried out on the effect of charge and rate of fusion between Sendal virus and phospholipid vesicles. See, e.g., Nir, Klappe, and Hoekstra, *Biochemistry* 25, pp. 6261–6266 (1989); and Stegmann, Nir and Wilschut, *Biochemistry* 28, pp. 1698–1704 (1989). Similarly, Huang et al., U.S. Pat. No. 4,789,633, used pH sensitive phospholipid materials to show the effect of pH on vesicle fusion.

The articles reporting vesicle/virus fusion with these model systems describe experiments carried out with phospholipid and/or glycolipid materials since they are used to model the action of cellular membranes. Normally, unilamellar vesicles are utilized as their cellular model. Since the experiments are directed to the mechanism of the vital insertion of nucleic acid, the reproductive activity of the fusion product is not normally tested. As such, there appears to be little data to determine whether these fusion products (or hybrids) could still infect other cells.

One problem in dealing with viruses is that they are not susceptible to classic antibiotics. This makes treatment of patients, as well as clinical experiments, difficult. Although certain chemotherapeutic agents and other chemoprophylactic drugs such as Acyclovir and Amantadine have been used against various viruses, they are not universally effective. Similarly, although it has been theorized that interferon might be useful in treating viral diseases, this has also not been overly successful.

Much of the clinical virus work has been directed to vaccines. However, little work has been carried out on vaccines using vesicles, and even less on anti-vital vaccines containing vesicles. To the extent there have been tests, they have been carried out using "killed" viruses. As such, this anti-viral work has used the vesicles solely as adjuvants. One example of this anti-viral vaccine is the Newcastle disease vaccine sold by Immunogenetics, Inc., a sister company of the assignee of the present application. This vaccine uses killed Newcastle disease virus in conjunction with non-phospholipid paucilamellar lipid vesicles.

As an adjunct to the work in connection with development of this Newcastle disease vaccine, the present inventors tested the effect of using live rather than killed viruses in conjunction with the vesicles as an immunizing agent. The purpose behind this type of work is that in certain circumstances, the live viruses make better immunizing agents than killed viruses. Surprisingly, not only did the live viruses work as immunizing agents, it appears that fusion took place between the non-phospholipid paucilamellar vesicles and the virus protein envelope. Although fusion between phospholipid vesicles and virus coatings were known, it is unexpected that non-phospholipid vesicles could fuse since there is a large difference between the properties of a phospholipid membrane such as is used in a conventional liposome and the non-phospholipid membranes. Phospholipids have a dual carbon chain structure as compared with the singular carbon chains used in the non-phospholipid vesicles.

Even more interesting, the fusion product of the paucilamellar non-phospholipid vesicles and the virus appeared not to be infectious; that is, the fusion appeared to denature the nucleic acid of the virus. Accordingly, this has opened a new realm of speculation and experimentation for the inventors.

The results uncovered by the present inventors in connection with the Newcastle disease vaccine has led to the possibility of a new method for prevention and treatment for vital infections. Accordingly, an object of the invention is to provide a treatment for vital infection using paucilamellar lipid vesicles.

Another object of the invention is to provide a method of preparing an anti-viral immunizing agent by combining an enveloped virus with paucilamellar lipid vesicles.

A further object of the invention is to provide a method of treating viral infections without affecting other cells.

Still further object of the invention is to provide a method of making a vaccine useful in treating viral infections.

These and other objects and features of the invention will be apparent from the following description and the claims.

SUMMARY OF THE INVENTION

The present invention features a method for inactivating enveloped viruses, both in vivo and in vitro, as well as anti-viral vaccines and virus inactivating solutions. The invention is based, in part, on the discovery that the combination of an enveloped virus and a paucilamellar, particularly non-phospholipid, lipid vesicle will form a complex that inactivates the virus nucleic acid.

The method of inactivating an enveloped virus, which has an outer proteinaceous or lipoproteinaceous coating surrounding an interior containing the nucleic acid necessary for replication of the virus, has the initial step of mixing the virus with paucilamellar, preferably non-phospholipid, lipid vesicles. Mixing of the vesicles and virus causes the outer coating of the virus and the lipid vesicles to fuse. This appears mediated by the fusion protein of the enveloped virus. Shortly after fusion, the nucleic acid from the virus begins to denature, thereby inactivating the virus. Although this method is effective for any enveloped virus, RNA viruses such as orthomyxoviruses, paramyxoviruses, retroviruses and HIV are preferred. If a DNA enveloped virus is used, herpesviruses and similar DNA viruses are preferred. The fusion reaction requires collision between the vesicles and the virus envelope, so the mixture may be agitated to insure collision and improve kinetics. Preferably, about one hundred vesicles per virus (or even more) are used to insure rapid kinetics of collision, but values as low as one vesicle per virus can be used. Preferred non-phospholipid materials for use in vesicles include polyoxyethylene fatty acid esters, polyoxyethylene fatty acid ethers, polyoxyethylene sorbitan esters, polyoxyethylene glyceryl mono and diesters, betaines, sarcosinamides, diethanolamides, long chain acyl hexosamides, long chain acyl amino acid amides, long chain acyl amides, glyceryl mono-and diesters, monomeric and dimeric alkyds, dimethyl acyl amines, $C_{12}$–$C_{20}$ fatty alcohols, $C_{12}$–$C_{20}$ glycol monoesters, $C_{12}$–$C_{20}$ fatty acids, N,N-dimethylamides, and mixtures thereof.

The inactivated virus has particularly advantageous use as a vaccine since the lipid vesicle-virus hybrid formed by this process can act as its own immunizing agent. This is accomplished because the proteinaceous coat of the virus supplies epitopes for immunization and the vesicle portion acts as an adjuvant.

Another aspect of the invention provides a method of inactivating an enveloped virus in vivo in a mammal. This method has the steps of providing a virus inactivating solution consisting of paucilamellar, preferably non-phospholipid, lipid vesicles in a pharmaceutically acceptable carrier and applying the solution topically proximate to an area where the virus occurs and infects. The concentration of the lipid vesicles must be sufficient so that they will fuse with the virus particles, thereby inactivating the virus nucleic acid. For example, a spray or other aerosol means of delivery to the nasal passages is particularly effective for dealing with influenza and other viruses which infect these passages. Other ways of topically applying the inactivating solution include creams, mouthwashes, gels such as vaginal gels, and lubricants such as condom lubricants. These latter categories are particularly effective for use against retroviruses such as the HIV virus.

The lipid vesicles used in this inactivation solution can be made of any of the non-phospholipid materials previously described and have either an aqueous solution in their central cavity or an oil-filled solution. Methods of manufacturing these vesicles, and the vesicles themselves, are described in more detail in U.S. Pat. No. 4,911,928, U.S. Pat. No. 5,147,723, U.S. Pat. No. 5,032,457, U.S. Pat. No. 4,895,452, and U.S. patent application Ser. No. 761,253, the disclosures of which are all incorporated herein by reference. In a most preferred embodiment of the invention, the vesicles carry a material which itself can assist in disrupting the nucleic acid of the virus. Of particular interest is the use of an RNAase or DNAase in the vesicles. Other materials which disrupt nucleic acids, such as binary amines and polyvalent aldehydes, may also be used so long as they do not disrupt or modify the vesicle structure itself. Negatively charged vesicles may have particularly advantageous effects in the fusion reaction with the viruses, so charge producing agents such as dicetyl phosphate or a carboxylic acid like oleic acid may also be incorporated in the vesicle wall. Similarly, the thermotropic phase transition may be modified by including a sterol such as cholesterol in the vesicle wall.

The invention also contemplates the inactivation solution itself. This inactivating solution is in the form of the paucilamellar lipid vesicles in a pharmaceutically acceptable carrier with an RNA (or DNA) degrading agent encompassed in the vesicles. An RNAase or DNAase would be the preferred nucleic acid degrading agent, but other agents could be used.

In still another aspect of the invention, the virus inactivating solution containing lipid vesicles is adsorbed or held on a carrier, preferably a fibrous carrier, which can then be used to provide sustained release of the solution. One of the examples of this carrier is a bandage or wipe which "weeps" the solution topically, thereby allowing sustained release of the inactivating solution and long-term anti-viral protection. This would be particularly useful as a prophylactic method for treating wounds or burns where viral infection is a particular problem.

The invention would be more apparent from the following detailed description.

DETAILED DESCRIPTION OF THE INVENTION

The present invention concerns a method of inactivating viruses without harming other cells. This method is based on the fusion of paucilamellar lipid vesicles and the virus envelope, with the attendant degradation of the viral nucleic acid. A viral inactivating system, which may include a material that further degrades the nucleic acid such as an RNAase or DNAase, is also disclosed.

While a number of studies have been carried out concerning the fusion of liposomes and virus cells, substantially no work has been conducted to uncover what happens to the virus nucleic acid after fusion. The present invention is based on the determination that after fusion of viruses with paucilamellar lipid vesicles, preferably those which have non-phospholipids as their primary lipid, the nucleic acid starts to denature and finally fragments. Although this degradation appears to be spontaneous, the addition of a nucleic degrading agent may assist in this process. Even if the degradation agent is merely released, such a release in the vicinity of other virus particles may degrade other virus particles. That is, the degrading agent may be able to cross the viral envelope and attack virus particles which have not fused by being localized near viruses which have not been subject to the degradation from the present invention.

The reaction between the vesicles in the inactivating solution of the present invention and the virus is very rapid. Within minutes after vesicle/virus contact, electron micrographs have shown that the virus membrane fuses the vesicle membrane. "Knobs" on the virus membrane, which have been identified as hemagglutinin glycoproteins and/or neuraminidases, distribute at the surface of the hybrid fusion membrane. The hybrid vesicle/virus forms a shape which appears to be a vesicle with a virus membrane "cap". The vital RNA (or DNA) expands and unfolds below the cap in an area that initially was vesicle. The RNA (or DNA) may fragment, furthering the degradation and confirming inactivation of the virus.

Enveloped viruses which may be used in the present invention include coronaviruses, herpesviruses, retroviruses such as human immunodeficiency virus, paramyxoviruses such as Sendal virus and rhabdoviruses. All of these viruses have fusion proteins which are very similar and therefore may be useful in the present invention.

The following Examples will more clearly illustrate the invention and its efficacy.

EXAMPLE 1

In this Example, Newcastle disease virus, a common poultry virus, was fused with a variety of different non-phospholipid paucilamellar lipid vesicles. The vesicles were all made using the general procedures set forth in U.S. Pat. No. 4,911,928. Briefly, the lipid components of the vesicle walls were heated to a flowable state and placed in a first syringe. The aqueous component, in all these cases distilled water, was also heated and placed in a second syringe. The two syringes were connected by the stopcock and the materials were pushed back and forth through the stopcock for a minute or two until vesicles were formed. Table 1 lists the ingredients for each of the vesicle lots used in this experiment and the following two experiments.

TABLE 1

| Formula | Primary Lipid | Cholesterol | Charge Producing Agent |
|---|---|---|---|
| 101-1 | Cocylsarcosinate | + | — |
| 101-2 | Glyceryl dilaurate | — | Deoxycholic acid |
| 101-3 | Glyceryl distearate | — | Deoxycholic acid |
| 101-4 | Cetyl alcohol | + | Quaternary amine |
| 101-5 | Stearyl alcohol | + | Quaternary amine |
| 2571LO | Polyoxyethylene 2 cetyl ether | + | Oleic acid |
| 2563LO (061287A) (061287B) | Polyoxyethylene 2 cetyl ether | + | Dicetyl phosphate |

The lipid vesicles were blended with an aqueous medium into a vaccine which was serially diluted in 10-fold dilutions. The base vaccine had about $10^6$ vesicles/virus particle. These were then tested either ten minutes after mixing with the virus or after an overnight incubation at 4° C.

Testing was carried out by inoculating the test solution into five 9–11 day old embryonated eggs. Inoculation took place by punching holes in the top of the eggs and injecting 0.1 ml of the appropriate dilution per embryo into the allantoic cavity. Standard chicken eggs were the test subject, using a procedure normally used to test for Newcastle disease virus. The eggs were then sealed with glue, incubated for five days, and were candled daily to test for embryo viability.

At least four embryos per dilution were required to be viable at post-incubation for a test to be considered valid. On the fifth day of incubation, all the eggs were opened and the embryos were examined. The healthy embryos, e.g., those without the Newcastle disease, were much larger than those which had received Newcastle disease which were stunted or hemorrhaging.

The end point was tested by the presence of hemagglutination activity. To test hemagglutination activity, a small amount of the allantoic fluid is removed. 0.1 ml of the harvested fluid is placed in a microtiter plate and after making two-fold dilutions in saline, 0.1 ml of a 0.5% suspension of chicken erythrocytes is added. If hemagglutination is present, the sample is positive for virus growth while if no hemagglutination is observed, the sample is negative for Newcastle disease virus. Values are calculated in terms of $EID_{50}$/ml, which is the antilog of the highest dilution yielding a positive result.

Table 2 shows the results of this testing using all the formulations of vesicles shown in Table 1 at ten minutes after vaccine preparation (titer (A)) or after overnight storage (titer (B)) as well as the titer loss. The greater the titer loss, the more Newcastle disease virus that was killed.

TABLE 2

Newcastle Virus Assay of Novasome Vaccines
(Titer expressed as $EID_{50}$/ml)

| Lot # | Novasome I.D. | Titer (A) | Titer (B) | Titer Loss (total) |
|---|---|---|---|---|
| A. | 101-1 | <3.00/ml | <2.00/ml | >6.34/ml |
| B. | 101-2 | <3.00/ml | <2.00/ml | >6.34/ml |
| C. | 101-3 | 5.83/ml | 3.17/ml | 5.17/ml |
| D. | 101-4 | 8.69/ml | 7.00/ml | 1.34/ml |
| E. | 101-5 | 8.37/ml | >6.17/ml | <2.17/ml |
| F. | 2571LO | 8.80/ml | >6.12/ml | <2.22/ml |
| G. | 2563LO | 8.00/ml | >6.38/ml | <1.96/ml |
| H. | VIRUS CONTROL | 9.00/ml | 8.34/ml | 0.66/ml |

As is evident from these results, all of the vesicles reduced the Newcastle disease virus levels by at least 1.3 logs/ml. The negatively charged vesicles (B–C) and the zwitterionic vesicles (A) caused the highest loss of titer, showing more effective virus kill.

Based on the foregoing, it is clear that the mixing of the vesicles and virus will reduce virus activity.

EXAMPLE 2

In this Example, the ratio of virus particles to the paucilamellar vesicles was modified, using similar vesicle formulations described on Table 1. All dilutions are reductions in the vesicle:virus ratio. Formulations 061289A and 061289B are substantially identical to formulation 2563LO. The control virus, diluted 1:5, showed a greater than 9.17 titer immediately and greater than 9.24 titer overnight at 4° C. Table 3 shows the results of this experiment.

TABLE 3

| Novasome I.D. | Undiluted | 1:10 | 1:100 | 1:1000 |
|---|---|---|---|---|
| 101-1 | <2.00 | <2.00 | 6.31 | >9.17 |
| 101-2 | <2.00 | 6.66 | 8.83 | >9.37 |
| 061289A | >7.12 | >8.50 | >9.33 | 8.66 |
| 061289B | >7.50 | >8.40 | >9.17 | 8.69 |

As can be seen from Table 3, the sarcosinate and glyceryl dilaurate formulations provide excellent virus inactivation at the undiluted and 1:10 values while at 1:100, they still provide inactivation but it is more limited. In contrast, although the polyoxyethylene cetyl ether formulations show degradation of the Newcastle disease virus at the undiluted form, it only provides limited protection at lower dilutions. This Example confirms, however, that there is internalization and degradation of Newcastle disease virus by the fusion process of the present invention.

EXAMPLE 3

In this Example, a different virus, laryngotracheitis virus, a fowl herpesvirus, was used in place of the Newcastle disease virus. Substantially the same procedure was used as is described in Examples 1 and 2 except the antibodies to the herpesvirus replaced the antibodies to the Newcastle disease virus.

Table 4 shows results of this experiment.

TABLE 4

| | Herpesvirus Assay of Novasome Vaccines (Titer Expressed as $EID_{50}/ML$) | | | |
|---|---|---|---|---|
| Loss Lot # | Novasome I.D. | Titer (A) | Titer (B) | Titer (total) |
| A. | 101-1 | <2.00 | <2.00 | >3.29 |
| B. | 101-2 | <2.00 | <2.00 | >3.29 |
| C. | 101-3 | <2.00 | <2.00 | >3.29 |
| D. | 2571LO | 3.91 | 3.40 | 1.38 |
| E. | 2563LO | 3.20 | 3.70 | 2.09 |
| F. | VIRUS CONTROL | 5.29 | 4.06 | 1.23 |

Although the virus control has a much lower titer and the loss on the virus control of activity is greater overnight, it is clear that the fusion of the virus and lipid vesicles degrades the virus greatly. As such, this verifies that more than a single type of virus may be used in the present invention.

The foregoing examples are meant to be merely exemplary and not limiting in any way. The present invention is defined by the following claims and reasonable or obvious modifications and variations thereof will be understood to be included by those skilled in the art within those claims.

What is claimed is:

1. A method of inactivating an enveloped virus in vitro, said enveloped virus having an outer coating of a proteinaceous or lipoproteinaceous material surrounding an interior containing nucleic acid necessary for replication of said enveloped virus, said method comprising the steps of:

mixing said enveloped virus with at least one paucilamellar lipid vesicle substantially free of DNAses and RNAses and having non-phospholipids as constituting the greatest proportion, by weight, of any single lipid material forming the bilayers of said lipid vesicle and wherein said non-phospholipids are selected from the group consisting of cocylsarcosinate, glyceryl dilaurate, glyceryl distearate, cetyl alcohol, stearyl alcohol, and polyoxyethylene 2 cetyl ether;

allowing said enveloped virus and said non-phospholipid paucilamellar lipid vesicle to be kept in contact until said outer coating of said enveloped virus and said bilayers of said lipid vesicle fuse; and allowing said nucleic acid of said fused enveloped virus to denature, thereby inactivating said enveloped virus.

2. The method of claim 1 wherein said mixing step comprises agitation of said enveloped virus and said paucilamellar lipid vesicle.

3. The method of claim 1 wherein said mixing step comprises mixing approximately 1–100 paucilamellar lipid vesicles per enveloped virus particle.

4. The method of claim 1 wherein said enveloped virus is an RNA virus having RNA as said nucleic acid.

5. The method of claim 4 wherein said RNA virus is selected from the group consisting of orthomyxoviruses, paramyxovirus, coronaviruses, and retroviruses.

6. The method of claim 1 wherein said enveloped virus is a DNA virus.

7. The method of claim 6 wherein said DNA virus is a herpesvirus.

* * * * *